United States Patent
Akopov

[11] 3,951,138
[45] Apr. 20, 1976

[54] DEVICE FOR GRIPPING SOFT TISSUES DURING SURGICAL INTERVENTION

[76] Inventor: Ernest Mikhailovich Akopov, Dubninskaya ulitsa, 61, kv. 88, Moscow, U.S.S.R.

[22] Filed: July 24, 1974

[21] Appl. No.: 491,515

[30] Foreign Application Priority Data
July 26, 1973 U.S.S.R. .............................. 1954521

[52] U.S. Cl. ................................. 128/17; 128/337; 128/346; 24/263 PJ
[51] Int. Cl.² .................... A61B 1/32; A61B 17/08; A61B 17/00
[58] Field of Search ............... 128/17, 20, 325, 329, 128/334 R, 334 C, 335, 336, 337, 346, 361, 303 R; 24/87 R, 87 C, 88, 150 R, 158 S, 162, 243 FS, 263 PJ, 263 FC, DIG. 22, 73 HS; 81/1 R–1 N, 3 R, 15.2–15.3; 17/66, 70

[56] References Cited
UNITED STATES PATENTS

| | | | |
|---|---|---|---|
| 268,632 | 12/1882 | Danforth | 128/337 |
| 535,798 | 3/1895 | Hawkes | 128/335 |
| 1,601,035 | 9/1926 | Nauth | 128/346 |
| 2,516,359 | 7/1950 | Zoller | 24/DIG. 22 |
| 3,083,711 | 4/1963 | Ramsay | 128/325 |
| 3,601,127 | 8/1971 | Finegold | 128/337 |

FOREIGN PATENTS OR APPLICATIONS

| | | | |
|---|---|---|---|
| 418,970 | 10/1910 | France | 128/337 |
| 461,207 | 2/1937 | United Kingdom | 128/303 R |

*Primary Examiner*—Robert W. Michell
*Assistant Examiner*—Rick Opitz
*Attorney, Agent, or Firm*—Holman & Stern

[57] ABSTRACT

A device for gripping soft tissues during surgical intervention, which comprises two plates adjoining each other by way of the lateral surfaces thereof and adapted to move one along the other. The face of the longitudinal edge of one plate is provided with straight fixing needles arranged in perpendicular relationship with said face, whereas the face of the longitudinal edge of the other plate which is proximate to the face with the straight fixing needles is provided with fixing needles curved in one and the same direction opposite to the direction of withdrawal of the device from the operation wound. A clamp for clamping and immobilizing tissues and organs is composed of two halves each comprising a jaw bearing the proposed device for gripping soft tissues.

9 Claims, 17 Drawing Figures

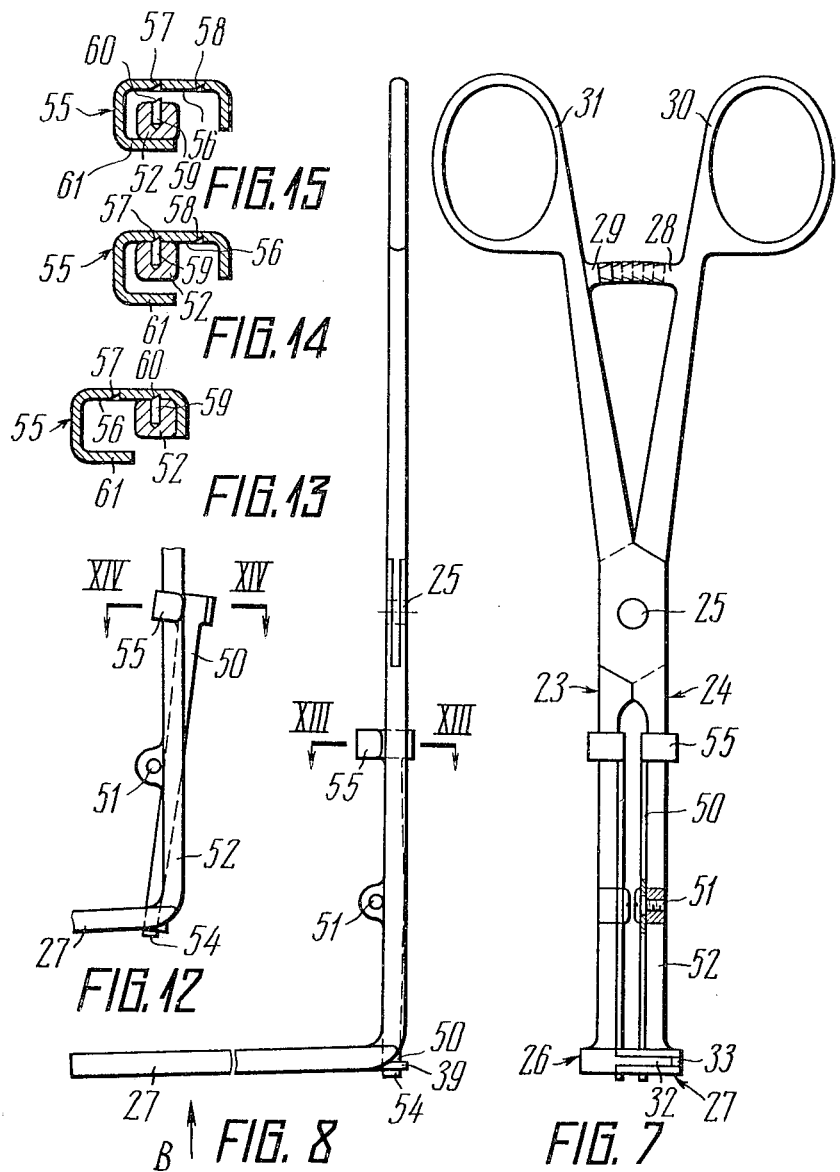

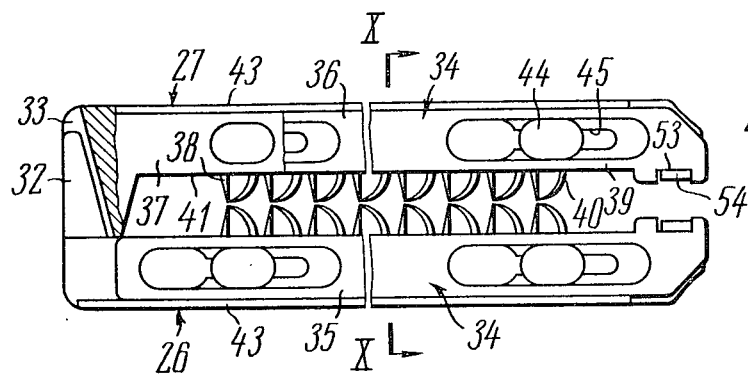
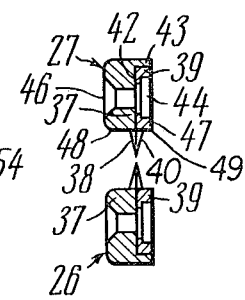
FIG. 9  FIG. 10
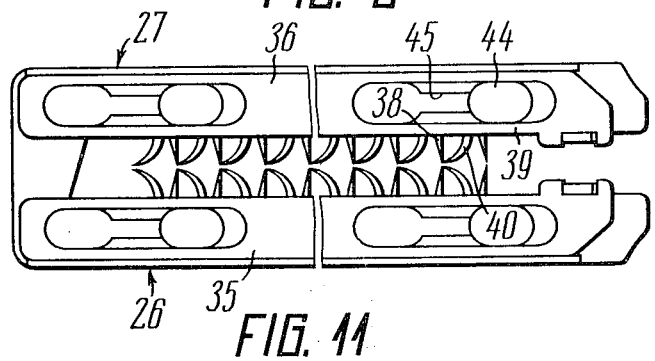
FIG. 11
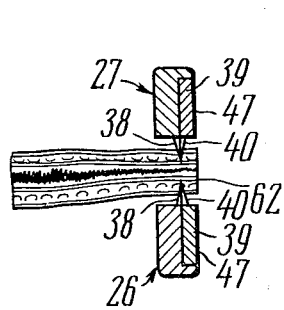 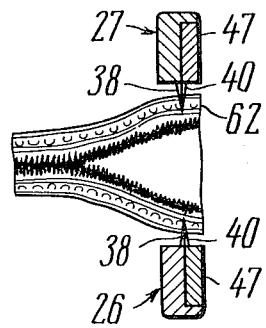
FIG. 16  FIG. 17

DEVICE FOR GRIPPING SOFT TISSUES DURING SURGICAL INTERVENTION

BACKGROUND OF THE INVENTION

The present invention relates to medical equipment and, more specifically, to devices for gripping soft tissues during surgical intervention. The proposed device may be employed for fixing the walls of an organ or tissues with a view to performing certain manipulations therewith, for example, for gripping the walls of a hollow organ by the surface layers thereof, setting them apart and maintaining them apart, or for gripping and turning the edges of dissected tissues, or for moving the edges of dissected tissues in a prescribed direction. The proposed device may be employed, inter alia, in stitching surgical apparatus, viz, apparatus for suturing hollow organs, e.g., in applying intestinal anastomoses. The proposed device may be employed in other surgical instruments as well, for example, in clamps for gripping intestinal walls or the wall of the bladder, in wound expanders, which are required, according to the conditions of surgical intervention, to stay outside of the wound cavity and to grip the walls of the wound being expanded on one side only, viz, on the side of the surface layers.

There is known a device for gripping soft tissues during surgical intervention which is employed in an instrument for stitching intestines. This known device is disposed on the jaws of two clamps of the instrument for stitching intestines which comprises a suturing means composed of a staple magazine, a staple pusher and a die for clinching the staples. The known device for gripping soft tissues comprises two movable plates with cooperating paired fixing needles, a cover for fastening the plates to the jaws, and a slide for displacing the plates with the fixing needles. The plates with the fixing needles are mounted in recesses formed in each jaw of the instrument so as to adjoin each other by way of the lateral surfaces thereof. The fixing needles of both plates are spaced at equal intervals on the longitudinal faces of the plates and are so curved that the tips of the needles of one plate point in a direction opposite to that in which the needle tips of the other plate are oriented. With the plates in the initial position, the paired needles stay apart. The needles are set in the recesses formed in the clamp jaws.

The plates with the needles are provided with inclined slots of equal length, the inclined slots of one of the plates changing into longitudinal slots whose length is equal to the distance between the tips of the paired curved needles in the initial position. The length of the plate with the inclined and longitudinal slots is equal to the length of the recess formed in the jaw, and this plate is adapted to move only laterally with respect to the jaw. The length of the plate with the inclined slots is shorter than that of the recess, this latter plate being adapted to move both laterally and lengthwise with respect to the jaw. The slide is provided with projections entering the plate slots.

The slide and, accordingly its projections occupy two extreme positions relative to the plates with the needles; in one of these positions, the initial position, the tips of the paired curved needles are set apart and recessed in the clamp jaw, whereas in the other position they are closed and protrude from the jaw.

The known device for gripping soft tissues in the instrument for stitching intestines operates as follows.

After the tissues have been gripped between the jaws of one of the clamps, the slide is displaced, with the projections of the slide acting on the inclined slots of the plates with the needles so that both the plates simultaneously extend from the clamp jaw and the tips of the needles transfix the surface layers of the tissues. As the slide moves further, the shorter plate displaces lengthwise, with the slide projections displacing in the longitudinal slots of the other plate which at this instant is immobilized relative to the jaw. The paired needles of the plates have their pointed tips brought together, gripping the tissues in nodes.

While manipulating the clamps in order to juxtapose the organ walls being sutured as well as while manipulating the magazine, the pusher and the die in order to suture the juxtaposed walls, the device for gripping soft tissues fixes the walls of the organs relative to the clamp jaws. Upon completion of the suturing operation, the slide is moved back, with the paired needles of the cooperating plates moving apart and retracting into the clamp jaw, releasing the clamped walls of the organs.

The known device for gripping soft tissues has a disadvantage which consists in that the fixing needles of both cooperating plates are curved, the needle tips of one plate being oriented toward the needle tips of the other plate and set apart in the initial position of the plates. Hence it is sometimes impossible to disengage the device from the tissues or organ being fixed without damage thereto. After gripping tissues in the course of surgery and after the paired curved needles of the plates are moved apart to release the tissues being fixed, the tissues are drawn by the needles into the recesses of the jaws and gripped by the needles which point in the direction of withdrawal of the device from the operation wound. Thus, for the above-stated reasons, having sutured organs with the aid of the known instrument for stitching intestines comprising the above-described device for gripping soft tissues, it is sometimes impossible to avoid traumatizing the intestinal walls while withdrawing the instrument, for the needles of the clamp plates fail to release the tissues after fixing.

The particular design of the known device for gripping soft tissues with movable plates bearing fixing needles adapted to extend from the clamp jaws adds to the complexity of the device and requires an increased cross-sectional area of the clamp jaws, which constitutes a drawback when the limited size of the operation wound is considered. However, the unfavorable shape and arrangement of the paired needles of the plates necessitate a design whereby the needles are recessed in the clamp jaws in their initial position, though a device with permanently protruding needles would be much simpler in design, for otherwise the protruding sharpened needle tips are liable to traumatize the hands of the surgeon or operator in the course of cleaning and preparing the device for operation as well as the organs being fixed and the surrounding tissues. Besides, the device having protruding needles is difficult to handle, for while it is being brought to the tissues or organs to be fixed and established in a desired position, the needles cling to the tissues.

The shape of the sharp-tip fixing needles and their arrangement in the known device do not guarantee that hollow organs, e.g., intestines, the stomach or the bladder, are gripped only by way of the surface layers of the walls, without penetration into the cavity of the organ, in a wide range of organ wall thicknesses.

It is an object of the present invention to provide a device for gripping soft tissues during surgical intervention which would ensure secure fixing of tissues and releasing of the fixed tissues.

Another object of the present invention is to provide a device for gripping soft tissues during surgical intervention which would ensure absolute safety of the fixed and surrounding tissues and organs, as well as of the hands of the surgeon or operator cleaning and preparing the device for operation.

A further object of the invention is to provide a device for gripping soft tissues during surgical intervention which would ensure that the walls of organs are gripped only by way of the surface layers thereof, without penetration into the organ cavity, in a wide range of organ wall thicknesses.

Yet another object of the invention is to provide a device for gripping soft tissues during surgical intervention which would be simple in design and convenient to clean.

SUMMARY OF THE INVENTION

The foregoing objects are attained by a device for gripping soft tissues during surgical intervention, which comprises two plates adjoining each other by way of the lateral surfaces thereof and bearing fixing needles on the faces of the longitudinal edges thereof, said fixing needles being all spaced at equal intervals and said plates being adapted to displace one along the other, causing the fixing needles to pierce the surface layers of soft tissues and to grip same, in accordance with the invention, the fixing needles of one of the plates are made straight and arranged in substantially perpendicular relationship with the face of the longitudinal edge of the plate, whereas the fixing needles of the other plate are curved in one and the same direction opposite to the supposed direction of withdrawal of the device from the operation wound.

It is preferred that, with the plates being in their initial position, the straight and curved fixing needles should adjoin one another by way of the tips thereof, defining closed contours.

It is desirable that the straight and curved fixing needles adjoin one another at approximately right angles.

In a clamp means for clamping and fixing tissues and organs, comprising two halves each carrying a jaw provided with a means for fixing tissues, the jaw of one half being disposed opposite the jaw of the other half, and the halves being so interconnected as to permit the jaws to be brought together and moved apart, the means for fixing tissues on the jaw is formed as a device for gripping soft tissues constructed in accordance with the invention, the plates of said device being fastened to the jaw.

The plate with the straight fixing needles should preferably be rigidly secured on the clamp jaw, whereas the plate with the curved fixing needles should be movably mounted on the jaw.

It is desirable that a step be provided between the fixing needles and the lateral surface of the jaw serving as a guide for the cutting instrument in dissecting tissues.

The proposed device provides for secure gripping of tissues in fixing and as well as for release thereof after fixing, in no way traumatizing the tissues while the device is being withdrawn from the operation wound. As the cooperating fixing needles are made straight on one plate and curved on the other, the direction of curvature being opposite to that in which the device is withdrawn from the operation wound, and as the straight and curved fixing needles are arranged in the proposed fashion, the proposed device can be manipulated without traumatizing the hands of the surgeon or the fixed and surrounding tissues. The proposed device further provides for the gripping of tissues by way of only the surface layers thereof in a wide range of organ wall thicknesses.

As the plate with the straight needles is rigidly connected with the jaws of the clamp means in accordance with the invention, the clamp means design is quite simple; it is convenient in cleaning, and the clamp jaws have a minimized cross-section.

The proposed device for gripping soft tissues may likewise be employed in surgical suturing instruments essentially formed as a clamp whose jaws mount, along with a device for gripping soft tissues, a suturing instrument comprising a magazine for metal staples, a staple pusher and a die with recesses for clinching the staples. Use of the proposed device for gripping soft tissues in such instruments also permits the jaw cross-section to be considerably reduced and extends the scope of application of the surgical suturing instruments of this type.

BRIEF DESCRIPTION OF THE DRAWINGS

The invention will be further understood from the following detailed description of specific embodiments thereof, taken in conjunction with the accompanying drawings, wherein:

FIG. 7 illustrates a clamp means for clamping and fixing tissues and organs, in accordance with the invention;

FIG. 8 is a side elevation of a clamp means for clamping and fixing tissues and organs, in accordance with the invention;

FIG. 9 is a view taken along the arrow B in FIG. 8 of the clamp jaws set in the initial position;

FIG. 10 is a sectional view taken on line X—X in FIG. 9;

FIG. 11 is a view taken along the arrow B in FIG. 8 of the clamp jaws set in the tissue gripping position;

FIG. 12 shows the levers of the clamp means, in accordance with the invention, set in the working position;

FIG. 13 is a sectional view taken on line XIII—XIII in FIg. 8;

FIG. 14 is a sectional view taken on line XIV—XIV in FIg. 12;

FIg. 15 shows the position of the gripping lever handle as the gripping lever is being retracted from the lock means;

FIG. 16 is a schematic illustration of the position of the fixing needles in the walls of the organ being clamped, shown after the organ portion being excised has been cut off; and FIG. 17 is a schematic illustration of the position of the fixing needles at the instant the walls of a hollow organ are being drawn apart.

DETAILED DESCRIPTION OF THE INVENTION

Figure 1:
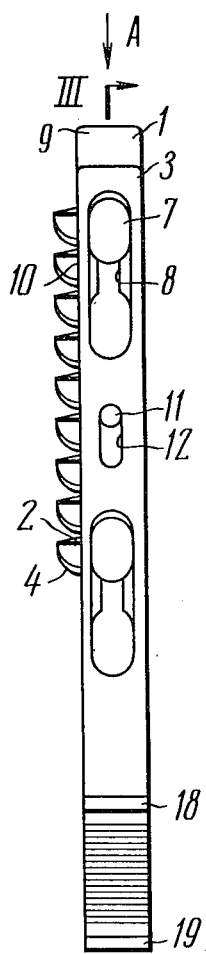
FIG. 1 illustrates a device for gripping soft tissues during surgical intervention shown set in the initial position, in accordance with the invention.
Figure 2:
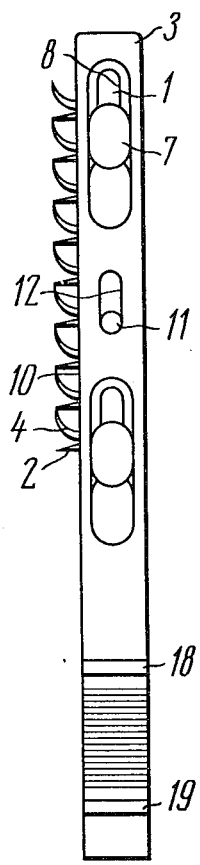
FIG. 2 illustrates a device for gripping soft tissues shown set in the tissue fixing position, in accordance with the invention.

Referring now to the drawings, it will be seen that the proposed device for gripping soft tissues during surgical intervention comprises a plate 1 (FIGS. 1 and 2) with fixing needles 2 and a plate 3 with fixing needles 4. The plates 1 and 3 adjoin each other by way of lateral surfaces 5 thereof (FIGS. 3 and 4) and are interconnected by means of guide pins 6 (FIG. 3) with heads 7. The pins 6 are rigidly secured on the plate 1 and enter longitudinal slots 8 formed in the plate 3. The fixing needles 2 and 4 (FIG. 1) are spaced at equal intervals on the faces of longitudinal edges 9 and 10 of the plates 1 and 3, respectively, which provides for the uniformity of gripping of tissues along the entire length thereof. Press-fitted into the plate 1 is a pin 11 which enters a closed aperture 12 in the plate 3, which aperture 12 limits the extent of displacement of one plate relative to the other one. The plates 1 and 3 are fixed in the extreme positions thereof by a projection 13 (FIG. 3) formed on the plate 1 which enters spherical depressions 14 and 15 in the plate 3 which are spaced by a distance equal to the length of the possible longitudinal displacement of the plates 1 and 3 and also corresponding to the spacing of the fixing needles 2 and 4 (FIG. 1). On the end of the plates 1 and 3 there are disposed respective projections 16, 17 (FIG. 3) and 18, 19 between which the operator places his fingers while handling the device.

The fixing needles 2 (FIG. 1) of the plate 1 are made straight and approximately perpendicular to the longitudinal edge 9. The fixing needles 4 of the plate 3 are curved, the tips thereof pointing in a direction opposite to that in which the ends of the plates 1 and 3 with the projections 16, 17 (FIG. 3) and 18, 19, respectively, are oriented, said projections being used to handle the device for gripping soft tissues. Hence, the tips of the curved fixing needles 4 are oriented oppositely to the direction of motion of the device being disengaged from the tissues and withdrawn from the operation wound.

With the plates 1 and 3 (FIG. 1) being in the initial position, the straight fixing needles 2 and the curved fixing needles 4 adjoin one another by way of the tips thereof, defining closed contours and thereby eliminating any possibility of traumatizing the operator's hands as well as the fixed and surrounding tissues while the device is being manipulated. In their working position (FIG. 2), the plates 1 and 3 are displaced from the initial position by a distance equal to the spacing of the fixing needles 2 and 4, the curved fixing needles 4 being displaced relative to the straight fixing needles 2 with which they have been in contact in the initial position likewise by a distance equal to the spacing of the fixing needles, so that the curved fixing needles 4 adjoin, by way of the tips thereof, the proximate straight fixing needles 2 of the plate 1.

The straight fixing needles 2 and the curved fixing needles 4 may adjoin one another at various angles, including acute angles. However, with a view to limiting the depth of penetration of the fixing needles into the tissues and ensuring that the tissues are gripped only by way of the surface layers thereof whatever the tissue thickness may be, the fixing needles 2 and 4 adjoin one another at approximately right angles, i.e., the tips of the curved fixing needles 4 are in approximate parallelism with the longitudinal edge 10 of the plate 3. The depth of penetration of the fixing needles 2 and 4 into the surface layers of tissues may likewise be set by adjusting the distance from the tips thereof to the face of the longitudinal edges 9 (FIG. 1) and 10 of the plates 1 and 3.

The device for gripping soft tissues operates as follows.

Figure 3:
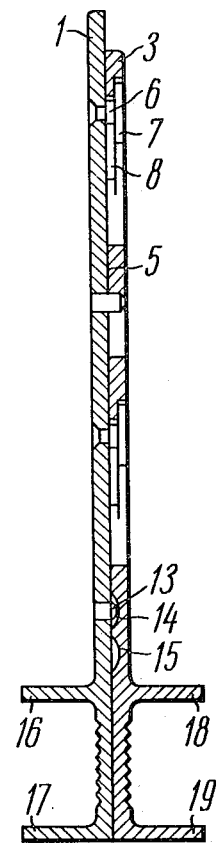
FIG. 3 is a sectional view taken on line III—III in FIG. 1.
Figure 5:
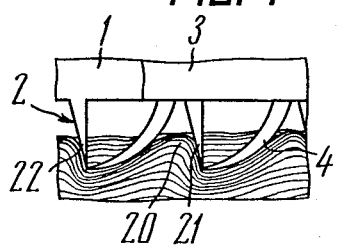
FIG. 5 is a schematic illustration showing the fixing needles of a device for gripping tissues, in accordance with the invention, being pressed to the tissues on the side of the surface layers.
Figure 6:
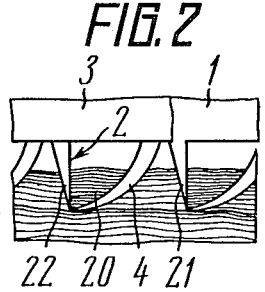
FIG. 6 is a schematic illustration of the fixing needles of a device for gripping tissues, in accordance with the invention, shown at the instant of fixing tissues.
Figure 4:
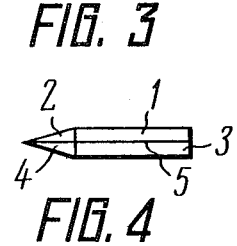
FIG. 4 is a view taken along the arrow A in FIG. 1.

The plates 1 and 3 of the device are set in the initial position as shown in FIGS. 1 and 3 are pressed to the surface of the tissues to be fixed. This causes the straight and curved fixing needles 2 and 4, adjoining one another in the initial position, to be imbedded in the tissues so that rolls 20 (FIG. 5) of tissue are formed therebetween. As the operator's fingers move the plate 3 with the curved fixing needles 4 relative to the plate 1 with the straight fixing needles 2 until the closed aperture (FIG. 2) is abutted against the pin 11, the tips of the curved fixing needles 4 transfix the rolls 20 (FIG. 6) of tissue and reach their extreme position to adjoin the straight fixing needles 2 with which these curved fixing needles have been in contact in the initial position. Thus, for example, if the fixing needle 4 in the initial position is in contact with a tip 21 (FIGS. 5 and 6) of the fixing needle 2, then, after the plate 3 has been displaced relative to the plate 1, this same fixing needle 4 comes to adjoin a tip 22 of the fixing needle 2. Thus are the tissues gripped between the straight fixing needles 2 and the curved fixing needles 4.

In the working position, the projection 13 (FIG. 3) of the plate 1 enters the spherical depression 15 of the plate 3 and immobilizes the plates 1 and 3, preventing their mutual displacement and additionally preventing the straight fixing needles 2 (FIG. 2) and the curved fixing needles 4 from moving apart. The device which has fixed the tissues on the side of the surface layers enables the various prescribed manipulations involved in a given surgical operation to be performed on the tissues.

In order to release the fixed tissues, the plate 3 with the curved fixing needles 4 is retracted to the initial position by acting on the projections 16, 17, 18 and 19 (FIG. 3) of the plates 1 and 3 disposed on the side of entry to the operation wound. While being retracted, the curved fixing needles 4 (FIG. 6), acting by the convex portions thereof, completely take the tissues off the straight fixing needles 2 with which the tips of the curved fixing needles are in contact in the initial position, defining closed contours. While the device is being withdrawn from the operation wound, the sharp tips of the curved fixing needles 4 do not cling to the tissues nor traumatize them on contact, for they are oriented oppositely to the direction of withdrawal of the device from the operation wound.

An exemplary application of the proposed device for gripping soft tissues during surgical intervention is in a clamp means for clamping and fixing tissues and organs. Such a clamp means comprises two halves 23 and 24 (FIG. 7) interconnected by means of a hinge 25. The halves 23 and 24 have at one end jaws 26 and 27 arranged in parallel relationship with the axis of the hinge 25, as indicated in FIG. 8, and at the other end toothed lugs 28 and 29 (FIG. 7) of a rack as well as ring-shaped handles 30 and 31. The jaw 26 is disposed opposite the jaw 27, and as the handles 30 and 31 are brought together or set apart, the jaws 26 and 27 close or move apart, respectively. To provide for proper alignment of the jaws 26 and 27, the jaw 26 is fitted on its end with a tooth 32 entering a slot 33 formed in the end of the jaw 27 (FIGS. 7 and 9).

Each of the jaws 26 and 27 is provided with a means 34 (FIG. 9) for fixing tissues, whereby the walls of organs can be gripped by way of the surface layers thereof and also drawn apart, if same should be required. Owing to this feature, the hollow organ portion to be excised can be cut off on the line of the jaws 26 and 27 of the clamp means and the walls of the remaining portion of the hollow organ in question can be drawn apart, giving access to the inner surface of the organ for visual inspection and for executing the required surgical intervention in the organ cavity.

The means 34 for fixing tissues comprises a device 35 for gripping soft tissues mounted on the jaw 26 and a device 36 for gripping soft tissues mounted on the jaw 27 (FIG. 9). The devices 35 and 36 are each formed as a plate 37 with straight fixing needles 38 and a plate 39 with curved fixing needles 40. The plates 37 with the straight fixing needles 38 are made integral with the jaws 26 and 27, the fixing needles 38 being disposed on the side of clamping longitudinal edges 41 of the clamp means. The plate 39 with the curved fixing needles 40 adjoins a lateral surface 42 (FIG. 10) of each jaw 26 and 27. The fixing needles 40 (FIG. 9) are curved towards the ends of the jaws 26 and 27, i.e., in a direction opposite to the direction of displacement of the jaws 26 and 27 of the clamp means relative to the organ being fixed as the clamp means is being withdrawn from the operation wound.

As the fixing needles 38 and 40 are made open, the jaws 26 and 27 of the clamp means with said devices 35 and 36 for gripping tissues are easy to clean and wash, for the devices 35 and 36 of the clamp means need not be disassembled specially for this purpose after each operation. Since the plates 37 and 39 with the fixing needles 38 and 40 need not be adapted to move out of the jaws 26 and 27 of the clamp means, the design of the jaws 26 and 27 can be largely simplified and their cross-section reduced. At the same time, however, the design of the devices 35 and 36 for gripping tissues, which are being discussed, allows the use of plates with fixing needles which do have an ability to move out of the jaws of the clamp means (not shown).

The jaws 26 and 27 are made with a flanged edge 43 (FIG. 10) serving to support the plate 39 while clamping tissues and with T-shaped guide projections 44 (FIGS. 10 and 11) which cooperate with longitudinal slots 45 (FIGS. 9 and 11) formed in the plates 39 and serve to guide them as they displace longitudinally with respect to the plate 37. The straight fixing needles 38 and the curved fixing needles 40 are disposed on the plates 37 and 39 at equal intervals and adjoin one another by way of the tips thereof, defining closed contours. Owing to this feature, it is practically impossible to traumatize the surgeon's hands, the tissues being clamped while positioning them between the jaws 26 and 27 of the clamp means, or the surrounding tissues in the operation wound, in spite of the fact that the fixing needles 38 and 40 of the devices 35 and 36 for gripping tissues permanently extend beyond the clamping longitudinal edges of the jaws 26 and 27 of the clamp means. There are steps 48 and 49 provided between the fixing needles 38 and 40, on the one hand, and the lateral surfaces 46 and 47 (FIG. 10) of the jaws 26 and 27 which serve for guiding the cutting instrument should the clamp means be employed for fixing the walls of an organ with the subsequent cutting off of a portion of the organ on the line of the jaws 26 and 27 of the clamp means. Owing to the presence of the steps 48 and 49, the cutting instrument passes at a certain distance from the fixing needles 38 and 40, the organ walls are securely fixed after the excision of the portion to be cut off, and the tissues clamped between the jaws 26 and 27 are prevented from moving about close to the fixing needles 38 and 40 and being pierced thereby while the jaws 26 and 27 are moved apart to open the organ cavity.

Each plate 39 with the curved fixing needles 40 is actuated by a lever 50 (FIGS. 7 and 12) which turns about an axle 51 secured on an elongated portion 52 of each half 23 and 24 (FIG. 7) of the clamp means. The plate 39 (FIG. 9) has a slot 53 receiving one end 54 of the lever 50 (FIG. 8). The other end of the lever 50 is formed as a curved handle 55 (FIG. 7) in whose surface 56 (FIGS. 13, 14 and 15) there are formed two depressions 57 and 58 (FIG. 15) for immobilizing the lever 50 (FIG. 7) in the initial position, as shown in FIG. 13, and in the working position, as shown in FIG. 14, by means of a lock means 59. The lock means 59 has an inclined surface 60 (FIG. 15) corresponding to the inclined surface of the depressions 57 and 58 on the handle 55. The bent end 61 of the handle 55 is spaced from the elongated portion 52 by a distance exceeding the height of the lock means 59. As pressure is applied to the bent end 61 of the handle 55 and the latter moves until abutment towards the elongated portion 52, the lever 50 (FIG. 7) flexes, causing the depression 57 (FIG. 15) to come out of engagement with the lock means 59. With the handle 55 so positioned, the lever 50 (FIG. 7) can be retracted to the initial position, drawing the fixing needles 40 (FIG. 10) clear of the fixing needles 38 as the plate 39 is moved to the initial position (FIG. 9).

Devices for gripping soft tissues of the clamp means being discussed may be made without special drives, as the device in FIG. 1. In such a case the bringing together and setting apart of the straight and curved fixing needles must be effected by displacing the plates bearing the curved fixing needles relative to the jaws of the clamp means.

The clamp means for clamping and fixing tissues and organs operates in the follows manner.

Having expanded the jaws 26 and 27 of the clamp means by setting the handles 30 and 31 (FIG. 7) apart, the jaws 26 and 27 are caused to envelop, e.g., a hollow organ and clamp same, the curved and straight fixing needles 38 and 40, which are joined with the movable plates 39 (FIG. 9) in the initial position, being imbedded into the organ walls (FIG. 16) on the side of the surface layers thereof. The levers 50 are rotated with the aid of the handles 55 (FIG. 12) clockwise until abutment, causing the end 54 of the lever 50 to drive the plate 39 with the curved fixing needles 40 (FIG. 16) to the working position, so that the curved fixing needles 40 transfix the walls of the organ and fix them by adjoining the stationary straight fixing needles 38. Then the portion of the organ which is to be excised is cut off on the line of the external surface 47 of the plates 39, if same should be required by the operation strategy, whereupon the jaws 27 and 26 of the clamp means are drawn apart to examine the internal cavity and perform therein all the necessary manipulations, as is shown in FIG. 17. A portion of tissues is left intact between the edge 62 of the cut organ wall and the fixing needles 40, which portion of tissues provides for the secure fixing of the walls and prevents the fixing needles from cutting through the tissues after the dissection stage.

In order that the fixed organ may be released after surgical intervention, the surgeon presses two fingers of his hand simultaneously on the bent ends 61 (FIG. 15) of the handles 55 (FIG. 12) of the levers 50 and drives them until abutment against the elongated portions 52 of the halves of the clamp means, turning the lever 50 to the initial position (FIG. 7). This causes the plate 39 (FIG. 9) to be drawn to the initial position, retracting the curved fixing needles 40 from the straight fixing needles 38 and thereby releasing the fixed tissues. While the jaws 26 and 27 of the clamp means are being withdrawn from the operation wound no damage is inflicted on the walls of the operated organ, since the fixing needles 40 of the devices for gripping tissues point in a direction opposite to the direction of withdrawal of the jaws 26 and 27 from the operation wound, while the straight fixing needles 38 adjoin the curved fixing needles 40.

What is claimed is:

1. A device for gripping soft tissues during surgical intervention, which comprises: two elongated plates adjoining each other along their side faces and connected to each other and having substantially flat edges normal to said side faces of said elongated plates, said plates being movable longitudinally relative to each other; straight fixing needles secured on the face of one longitudinal edge of one of said plates at equal intervals and arranged in approximately perpendicular relationship with said face; fixing needles secured on the face of the longitudinal edge of the other of said plates, disposed proximate to said face of the former plate which carries said straight fixing needles, and curved in one and the same direction opposite to the supposed direction of withdrawal of said device from the operation wound, said curved fixing needles being spaced at the same equal intervals as said straight fixing needles; and as one of said plates displaces along the other, said fixing needles transfix the surface layers and grip the soft tissues to be clamped.

2. The device as set forth in claim 1, wherein with said elongated plates being in the initial position, said straight and curved fixing needles adjoint one another by way of the tips thereof, defining closed contours, the tips of both the straight and curved fixing needles being at equal distance from one longitudinal edge of one of said elongated plates.

3. The device as set forth in claim 2, wherein said tips of said straight and curved fixing needles adjoin one another at approximately right angles.

4. A clamp means for clamping and fixing tissues and organs, comprising: two elements; a jaw of each element, said jaw of one of said elements being disposed opposite said jaw of the other of said elements, and said elements being so interconnected as to enable said jaws to be brought together and set apart; a device for gripping tissues provided on each of said jaws; two elongated plates of said device adjoining each other along their side faces and connected to each other and having substantially flat edges normal to said side faces, one said plate being rigidly secured on said jaw, whereas the other said plate being movable lengthwise to said plate being rigidly secured; straight fixing needles fastened to the face of the longitudinal edge of said plate at equal intervals facing the juxtaposed said jaw and arranged in approximately perpendicular relationship with said face; fixing needles fastened to the face of the longitudinal edge at equal intervals, which is disposed proximate to said face of said plate bearing said straight fixing needles, curved in one and the same direction opposite to the supposed direction of withdrawal of said jaw from the operation wound; said curved fixing needles being spaced at the same equal intervals as said straight fixing needles.

5. The clamp means as claimed in claim 4, wherein a step is provided between said fixing needles and the free side face of said jaw.

6. The clamp means as set forth in claim 5, wherein, with said plates being in the initial position, said straight and curved fixing needles adjoin one another by way of the tips thereof, defining closed contours, the tips of both the straight and curved fixing needles being at equal distance from one longitudinal edge of one of said elongated plates.

7. The clamp means as set forth in claim 6, wherein said straight and curved fixing needles adjoin one another by way of the tips thereof at approximately right angles.

8. The clamp means as set forth in claim 4, wherein with said plates being in the initial position, said straight and curved fixing needles adjoin one another by way of the tips thereof, defining closed contours, the tips of both the straight and curved fixing needles being at equal distance from one longitudinal edge of one of said elongated plates.

9. The clamp means as set forth in claim 8, wherein said straight and curved fixing needles adjoin one another by way of the tips thereof at approximately right angles.

* * * * *